US006517593B1

(12) United States Patent
Robertson et al.

(10) Patent No.: US 6,517,593 B1
(45) Date of Patent: Feb. 11, 2003

(54) MBI VORTEX BIOAEROSOL CASSETTE INSERT

(76) Inventors: Larry Don Robertson, 2484 Hwy. 39 N., Jewett, TX (US) 75846; Robert Allen Garrison, 1635 Mockingbird La., Southlake, TX (US) 76092

(*) Notice: Subject to any disclaimer, the term of this patent is extended or adjusted under 35 U.S.C. 154(b) by 0 days.

(21) Appl. No.: 09/641,503

(22) Filed: Aug. 21, 2000

(51) Int. Cl.[7] .............................. C12Q 1/04; C12Q 1/24

(52) U.S. Cl. .......................... 55/385.1; 96/286; 96/316; 96/327; 435/5; 435/7; 435/30; 435/34; 435/39

(58) Field of Search ..................... 95/216, 219; 96/286, 96/316, 327, 366; 73/28.01; 422/52; 435/30, 5, 7, 34, 39; 436/63, 172, 181; 55/385.1

(56) References Cited

U.S. PATENT DOCUMENTS

| | | | | |
|---|---|---|---|---|
| 3,564,843 A | | 2/1971 | Hirschler, Jr. et al. | |
| 3,980,563 A | | 9/1976 | Greutert et al. | |
| 4,249,655 A | | 2/1981 | Patureau et al. | |
| 4,606,232 A | | 8/1986 | Prodl | |
| 4,796,475 A | | 1/1989 | Marple | |
| 4,939,096 A | * | 7/1990 | Townell | 435/5 |
| 5,081,017 A | * | 1/1992 | Longoria | 435/30 |
| 5,254,147 A | | 10/1993 | Finke | |
| 5,690,825 A | * | 11/1997 | Parton | 435/34 |
| 5,701,012 A | * | 12/1997 | Ho | 250/461.2 |
| 5,773,710 A | * | 6/1998 | Squirrell | 73/28.01 |
| 5,855,652 A | * | 1/1999 | Tawey | 96/372 |
| 5,874,237 A | * | 2/1999 | Hull et al. | 435/34 |
| 5,898,114 A | | 4/1999 | Basch et al. | |
| 5,918,259 A | * | 6/1999 | Squirrell | 73/28.01 |
| 5,942,699 A | | 8/1999 | Ornath et al. | |
| 6,090,572 A | * | 7/2000 | Crosby | 435/34 |
| 6,101,886 A | | 8/2000 | Brenizer et al. | |
| 6,103,534 A | * | 8/2000 | Stenger et al. | 73/28.01 |
| 6,217,636 B1 | * | 4/2001 | McFarland | 96/327 |

FOREIGN PATENT DOCUMENTS

JP 407294393 A 11/1995

* cited by examiner

*Primary Examiner*—David A. Simmons
*Assistant Examiner*—Minh-Chau T. Pham
(74) *Attorney, Agent, or Firm*—Lowe Hauptman Gilman & Berner, LLP

(57) ABSTRACT

A cassette suitable for the sampling of ambient air to determine if it contains particulate matter made up of an in-port cap that has a detachable tubing extending therefore; an intake cap longitudinally attached to the in-port cap; a cassette insert longitudinally attached to the intake cap on a side thereof opposite to the side of the intake cap attached to the in-port cap; a filter assembly longitudinally proximate to an end of the cassette passageway opposite to the end attached to the intake cap, and in operative relationship with the cassette passageway such that air passing through the cassette passageway must pass through said filter; and air exit means longitudinally attached to the cassette insert and housing the filter assembly, wherein said cassette passageway comprises a substantially circular entry end proximate to said intake cap and an elongated end proximate to said filter assembly; wherein the intake cap has at least one internal passageway communicating with the detachable tubing and communicating with the passageway through the cassette insert, and wherein the exit means has at least one internal passageway that communicates, through the filter assembly, between the insert passageway and the ambient environment.

31 Claims, 3 Drawing Sheets

MBI VORTEX BIOAEROSOL CASSETTE INSERT

BACKGROUND OF THE INVENTION

Air sampling is used to quantify and qualify the contents of an environment. Laboratory analyses of the samples provide critical information relative to the potential exposure to harmful agents. Bioaerosol sampling focuses these processes on particles of biological origin. These agents include, but are not limited to, viable and non-viable fungal spores, bacteria, pollen, skin cells, fibers and insect parts.

The 25-millimeter (mm) cassette equipment with a 0.8 micron methylcellulose ester (MCE) filters are routinely used in the practice of industrial hygiene. More specifically, these cassettes are commonly used in the evaluation of airborne concentrations of asbestos. Bioaerosol agents can be recovered with the standard use of these cassettes, however; problems exist with regard to analyses of data collected by standard methodologies. Bioaerosol components are usually in far less airborne concentrations when compared to asbestos related industrial hygiene and/or abatement projects. Therefore, it becomes necessary to sample greater volumes of air in order to achieve appropriate detectable levels of bioaerosols using MCE filter technology. Airflow turbulence occur if 0.8-micron methylcellulose ester filters are exposed to air velocities over 15 liters per minute (L/m) that result in non-uniform particle distribution. Therefore, the rate of airflow cannot be adjusted over 15 L/m without potential damage to the MCE filter. Therefore, sample time is the only parameter available for manipulation. Under normal conditions, several hours of sampling are required in order to obtained an appropriate volume of air for bioaerosol analyses. These time constraints are problematic, especially when considering the costs related to on-site technical man-hours and/or the need for additional equipment for each individual sample location. The MBI Vortex Bioaerosol Cassette Insert has the unique ability to reduce sampling time to minutes without damaging MCE filters and thereby creating a highly efficient and effective bioaerosols recovery unit.

BRIEF SUMMARY OF INVENTION

The MBI Vortex Bioaerosol Cassette Insert is designed for a specific niche in the marketplace. Until recently, bioaerosol sampling has been performed using two basic types of collection methodologies; filtration and impact. Filtration methodologies utilize filter cassettes that are equipped with filters having a variety of design, components, and pore sizes. Typically most fungal bioaerosol components are above 1 micron in size. Hence, filters having a pore size just below 1 micron are useful in the filtration of fungal bioparticulate from the air without excessive air resistance. After collection, filters can be prepared for culture and/or viewed microscopically. The use of filters for fungal culture has proven to be inefficient with regard to recovery and is typically not recommended. Direct observation under microscope is possible, however; typically the sampling time required to collect detectable amounts rendered this sampling technique as implausible. Impacting methods have emerged as the principle means to evaluate airborne fungal bioparticulate. Impacting occurs directly onto agar-media surfaces for culture or on to special fixatives for direct microscopic examination. While some benefits exist with respect to culture recovery, the overall processes inherently introduces a bias of recovery and generally requires at least 5–7 days for incubation prior to analyses. Impacting directly on to special fixatives does allow the potential for an immediate analysis, however; some limits exist with regard to identification and classification.

Regardless, impaction methods remain vulnerable to a variety of parameters that effect "recovery efficiency". These factors include airflow, particle size, aerodynamics, etc . . . No impacting sampler is 100% efficient. Therefore, some percentage bioparticulate merely passes through the sampler and remains undetected.

Filtration technologies vastly improve recovery efficiency. The selection of filter pore sizes that are below the dimensions of fungal particulate ensures retention. Culture from filters have demonstrate relatively low recovery and are not generally recommended for air sampling, however; direct microscopic examination of filters offers an improved recovery efficiency over traditional impacting methods. In the past, direct filter examination has proven impractical because of the time required to collect samples, desiccation of recovered spores, as well as, increased man-hour and equipment costs. However, the MBI Vortex Bioaerosol Cassette Insert represents a new design that concentrates fungal bioparticulate into a distinct zone on the receiving filter. The concentration of recovered agents in effect reduces the collection area of the MCE filter thus allowing a reduction in sampling time without compromising detection levels or filter integrity. The MBI Vortex Bioaerosol Cassette Insert capitalizes on standard and accepted sampling methodologies, but now expands the use of 0.8 micron MCE filtration collection methodology into the field of fungal and other bioaerosol identification and reporting.

DETAILED DESCRIPTION OF THE DRAWINGS

Figure 1:
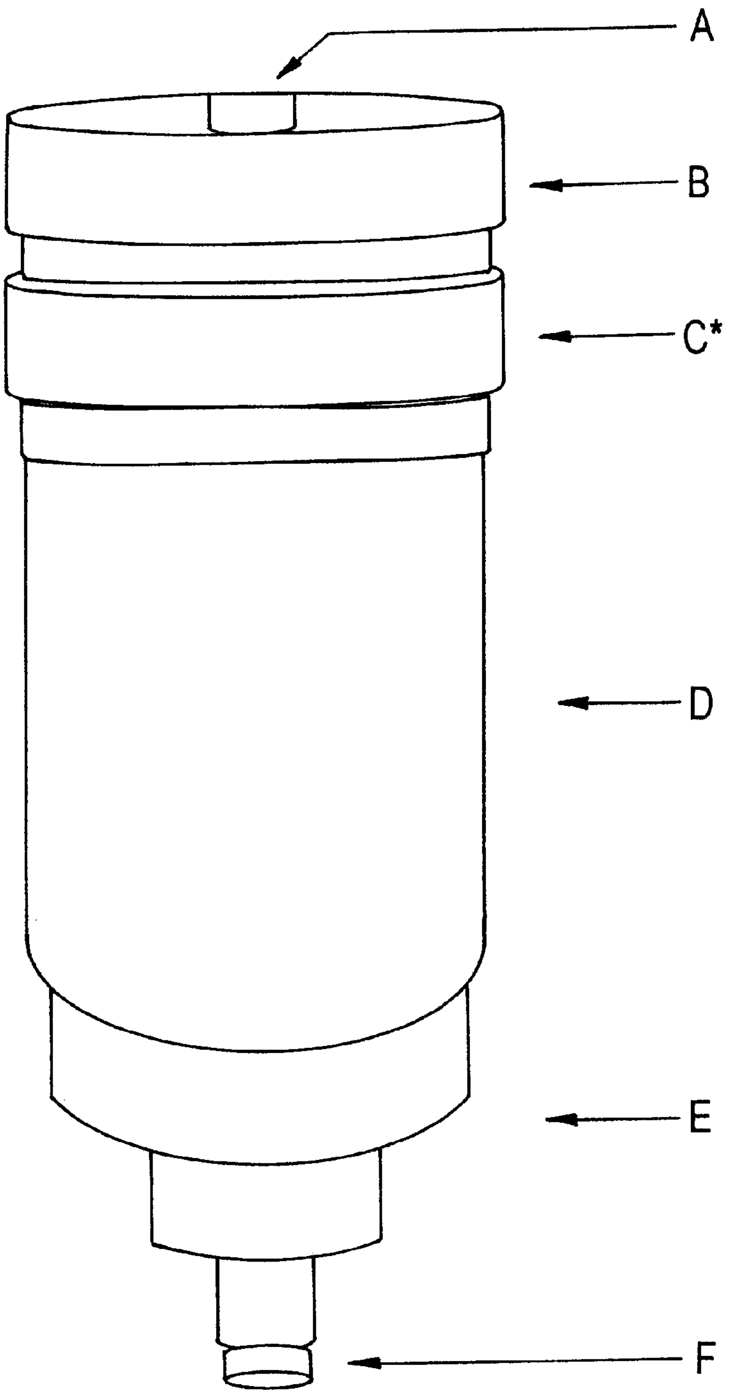
FIG. 1 depicts a standard 25-millimeter (mm) cassette containing the MBI Vortex Bioaerosol Cassette Insert.

FIG. 1 depicts a standard 25-millimeter (mm) cassette containing the MBI Vortex Bioaerosol Cassette Insert. The insert is wholly adaptable to existing designs and technologies utilizing 25-mm cassettes. Reference A identifies the in-port tubing cap. The tubing cap can be removed to allow the linking with tubing for remote collections in generally inaccessible spaces such as interstitial walls, crawl spaces, attics, etc . . . Reference B identifies the intake cap. The intake cap (B) is removed prior to the collection air and/or surface samples. The MBI Vortex Bioaerosol Cassette Insert (C) is attached to the cassette body tube (D) that is also attached to the filter canister (E). The filter canister contains a retention layer (H) supporting a 0.8-micron MCE filter (I) (not visible in this illustration). Reference F identifies the out-port tubing cap. The out-port tubing cap is removed to allow the attachment of a suction tube from a vacuum pump having a flow rate capacity between one (1) and fifteen (15) liters per minute. Operation of the vacuum pump draws air into the cassette. The MBI Vortex Bioaerosol Cassette Insert collects, funnels, concentrates, and deposit particulate onto the 0.8 micron MCE filter contained in the filter canister.

Figure 2:
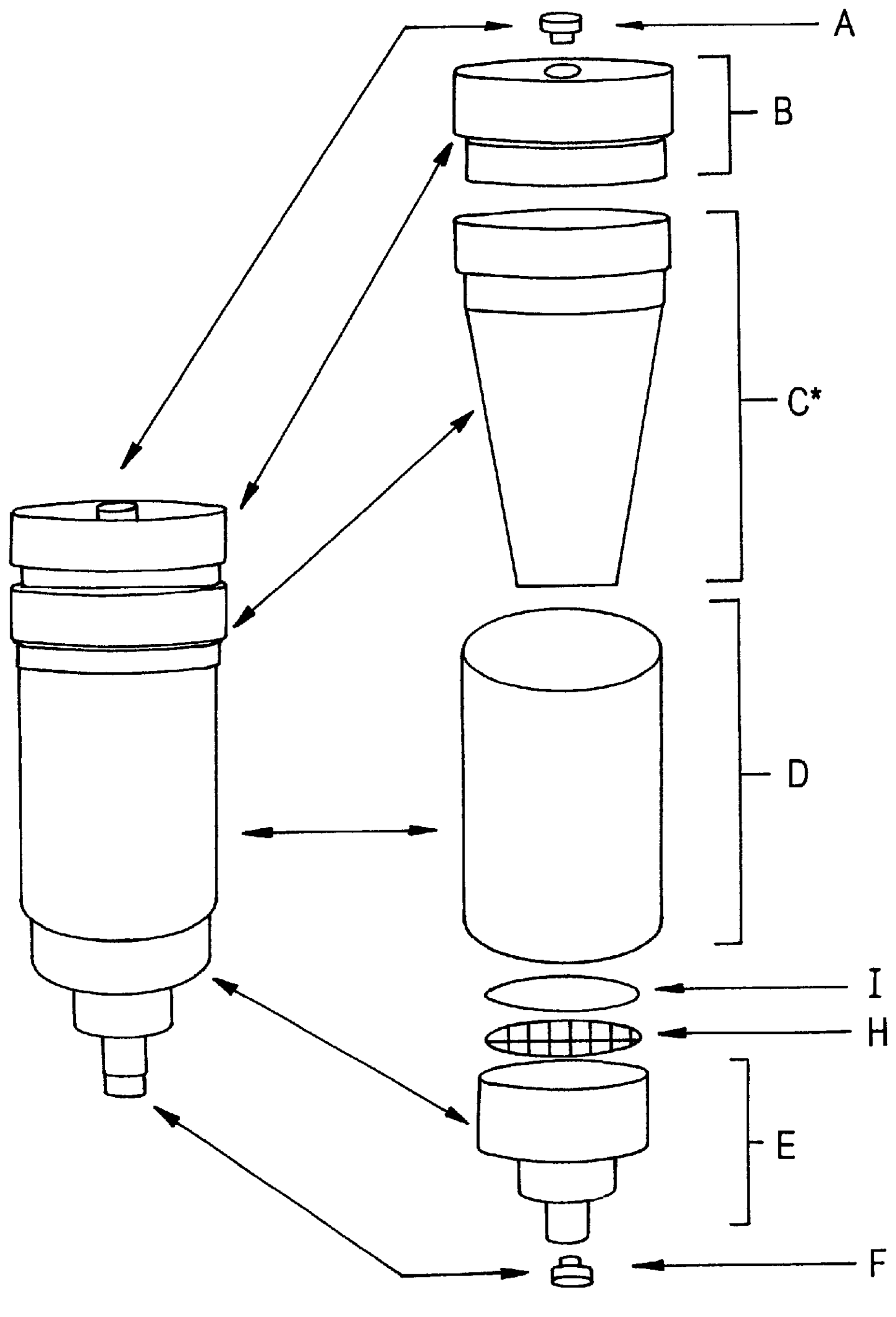
FIG. 2 is an exploded view of the 25-millimeter (mm) cassette containing the MBI Vortex Bioaerosol Cassette Insert.

FIG. 2 is an exploded view of the 25-millimeter (mm) cassette containing the MBI Vortex Bioaerosol Cassette Insert. The insert is wholly adaptable to existing designs and technologies utilizing 25-mm cassettes. Reference A identifies the in-port tubing cap. The tubing cap can be removed to allow the linking with tubing for remote collections in generally inaccessible spaces such as interstitial walls, crawl spaces, attics, etc . . . Reference B identifies the intake cap. The intake cap (B) is removed prior to the collection air and/or surface samples. The MBI Vortex Bioaerosol Cassette Insert (C) is attached to the cassette body tube (D) that is also attached to the filter canister (E). The filter canister contains a retention layer (H) supporting a 0.8-micron MCE filter (I). Reference F identifies the out-port tubing cap. The out-port tubing cap is removed to allow the attachment of a suction tube from a vacuum pump having a flow rate capacity between one (1) and fifteen (15) liters per minute. Operation of the vacuum pump draws air into the cassette. The MBI Vortex Bioaerosol Cassette Insert collects, funnels, concentrates, and deposit particulate onto the 0.8 micron MCE filter contained in the filter canister.

Figure 3:
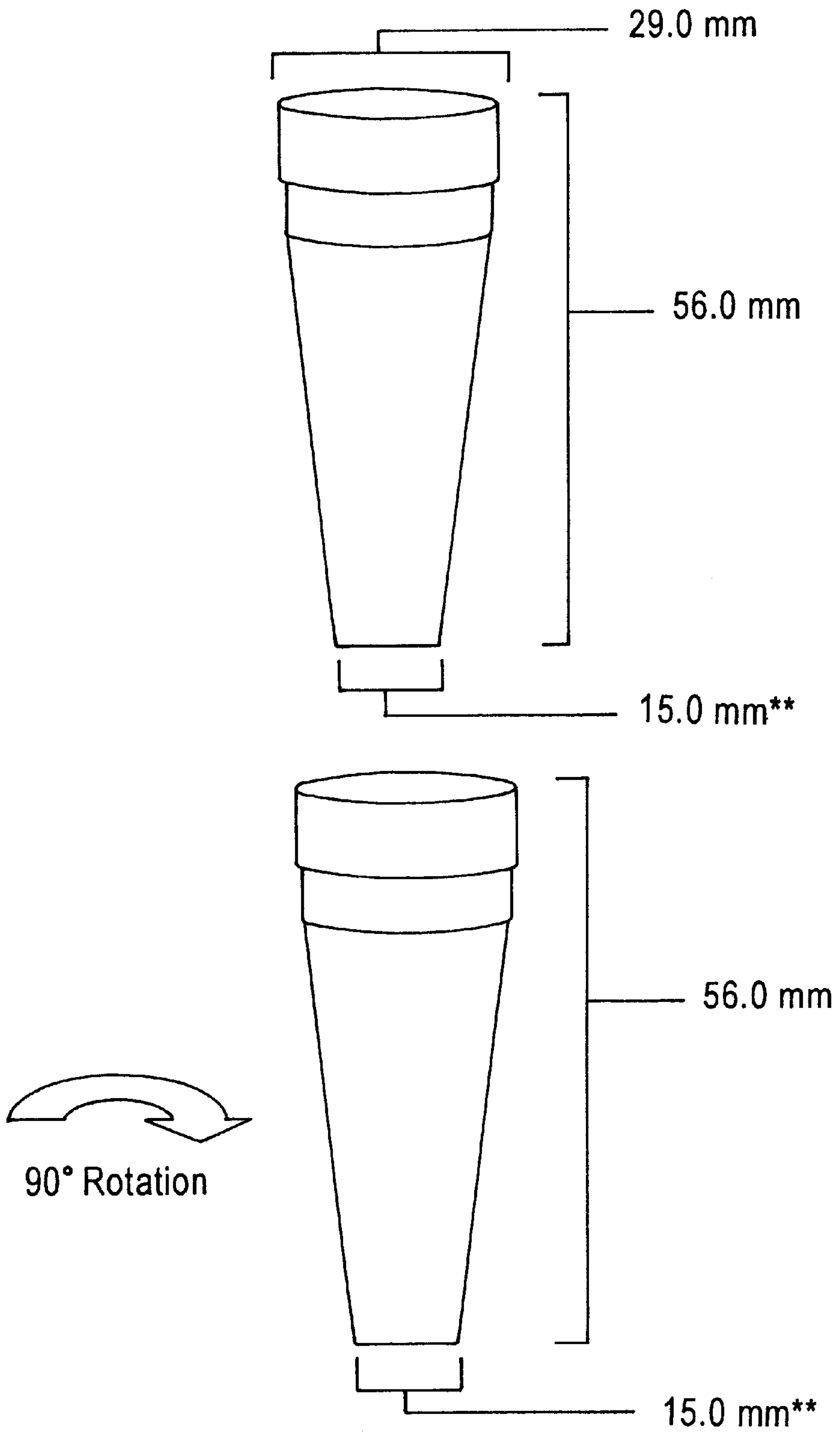
FIG. 3 are side views of the MBI Bioaerosol Cassette insert with general dimensions.

FIG. 3 are side views of the MBI Vortex Bioaerosol Cassette Insert with general dimensions. The opening of the MBI Vortex Bioaerosol Cassette Insert has a diameter of 29.0 millimeters (mm). The upper 16-mm has two distinct beveled layers. The upper layer is approximately 7.5 mm in length. The bottom 8.5-mm has been designed to allow insertion into the cassette body tube. Total length of the insert is 56.0 mm. The inner tube insertion has a design length of 40.0 mm which will terminate approximately 1–2 mm from the surface of the 0.8-micron MCE filter contained in the filter canister. However, the mechanism will be design such that the insert can actual touch the surface of the filter to enhance collection recovery under certain conditions. The insert begins as a circular structure that transitions into a vortex that narrows from top to bottom. The illustration indicates the bottom opening has outer diameter of 15.0 mm and generally designed to create a filter deposition trace having a diameter of 14–15 mm. However, these dimensions will vary in production, thus allowing the insert to specifically target particles of specific mass and aerodynamic character.

This, the present invention is well suited to carry out the objects and attained the ends and advantages mentioned herein. While the preferred embodiments of the present invention have been described for the purposes of this disclosure, changes in the design and arrangement of features can be made by these skilled in the art, which changes are encompassed within the spirit of this invention as defined by the appended claims.

What is claimed is:

1. A system for determining the content of solid particles in an ambient atmosphere, comprising an ambient gas and solid particles borne by said gas, wherein said system comprises a cassette comprising:

means to communicate between a cassette insert and an ambient atmosphere;

wherein said cassette insert comprises at least one internal passageway, wherein said at least one internal passageway collectively has a larger cross section entry end opening, adapted to communicate with said ambient atmosphere, and a smaller cross section exit end opening proximate to and not downstream of a filter;

wherein said filter is disposed in operative relationship with said cassette insert passageway such that substantially all ambient gas passing through said cassette insert passageway(s) passes through said filter;

suction means, disposed downstream of said filter, adapted to cause a fraction of the ambient atmosphere containing gas borne particles to pass through said cassette insert passageway and to cause substantially all of the fraction of the ambient atmosphere passing through said passageway to pass through said filter, and adapted to exhaust substantially all gas that has passed through said filter;

means for measuring the amount of solid particles disposed on said filter after said fraction of said ambient atmosphere has passed through said filter for a predetermined length of time; and means for determining the amount of solid particles contained on said filter.

2. The system as claimed in claim 1 wherein said upstream opening of at least one internal passageway is substantially circular and the downstream opening of said internal passageway is substantially elliptical, and wherein said filter medium is disposed across said elliptical opening.

3. The system as claimed in claim 1 wherein said downstream opening of at least one internal passageway is substantially rectangular, and wherein said filter medium is disposed across and in contact with said rectangular opening.

4. The system as claimed in claim 1 wherein said filter is spaced downstream from said downstream opening by up to about 2 mm.

5. The system as claimed in claim 1 wherein said cassette insert is disposed within a substantially cylindrical outer sleeve.

6. The system as claimed in claim 1 wherein said filter is juxtaposed said downstream opening and is attached across said downstream opening such that all of said fraction of said ambient atmosphere that passes through said cassette insert passes through said filter.

7. The system as claimed in claim 1 wherein said cassette insert is disposed within a substantially cylindrical outer sleeve that is functionally attached to an exit means.

8. The system as claimed in claim 1 further comprising a tubing adapted to communicate between said ambient atmosphere and at least one said internal passageway in said cassette insert, and further comprising means to force a fraction of said ambient atmosphere into said at least one internal passageway in said cassette insert through said tubing.

9. The system as claimed in claim 1 further comprising said filter being removable and replaceable.

10. The system as claimed in claim 9 wherein said filter is removable without causing a substantial proportion of the particles disposed thereon to be dislodged.

11. The system as claimed in claim 1 wherein said solid particles comprise mold spores.

12. The system as claimed in claim 11 wherein said ambient atmosphere comprises air containing suspended mold spores.

13. The system as claimed in claim 1 wherein at least one of said internal passageways has substantially smooth, gas impervious walls.

14. The system as claimed in claim 1 further comprising:

means for at least substantially reducing the number of particles, of a size that will be trapped by said filter, in said ambient atmosphere.

15. A system as claimed in claim 1 wherein said filter has a pore size of up to about 1 micron.

16. A system as claimed in claim 1 further comprising a microscope as the means of measuring the amount of solid particles entrapped on the filter.

17. A system as claimed in claim 1 wherein said particles are concentrated in a particular portion of said filter.

18. A system as claimed in claim 1 wherein said internal passageway comprises a substantially circular upstream end opening that transitions to a vortex that narrows from the opening end to the down stream end that is proximate to said filter.

19. A system, for sampling an ambient atmosphere or a surface to determine if it contains fungal elements, comprising:

an apparatus comprising:

A. a body section comprising an internal passageway;

B. a filter of a pore size that is adapted to entrap fungal elements thereon;

C. means to apply a suction to said apparatus whereby to:

1. cause a fraction of said ambient atmosphere, or a sample from said surface, to be drawn into said internal passageway,
2. concentrate said drawn fraction in said passageway,
3. dispose said drawn fraction, with said fungal elements concentrated therein, into operative association with said filter,
4. draw said concentrated fraction through said filter,
5. deposit fungal elements from said fraction on said filter; and
6. cause said drawn fraction, having at most a reduced amount of fungal elements therein, to exit said apparatus only after entirely passing through said filter; and means to determine the amount of fungal elements on at least a portion of said filter;

wherein:

said internal passageway reduces in cross section between an upstream end of said internal passageway and a downstream end of said passageway proximate to said filter, whereby being adapted to cause the fungal elements contained in said fraction to be concentrated from a more dispersed condition where said drawn fraction enters said internal passageway to a more concentrated condition proximate to said filter;

said internal passageway is adapted to communicate between said ambient atmosphere and said filter; and the combination of said suction means, said filter and said internal passageway are adapted to cause all of said drawn fraction to pass through at least a portion of said filter and to deposit a concentrate of fungal elements on at least that portion of said filter through which said concentrated drawn fraction passes.

20. A system as claimed in claim 19 wherein said apparatus further comprises:

an intake means, comprising an internal passageway of smaller cross section than the cross section of the upstream end of the internal passageway in said body section, communicating between said ambient atmosphere, or said surface, and an upstream end of said internal passageway.

21. A system as claimed in claim 20 wherein said intake means comprises tubing.

22. A system as claimed in claim 19 further comprising an entry port disposed between said ambient atmosphere, or said surface, and said upstream end of said internal passageway; wherein said entry port has a smaller cross section than the upstream end of said internal passageway.

23. A system as claimed in claim 19 wherein said filter has a pore size of up to about 1 micron.

24. A system as claimed in claim 19 further comprising a microscope as the means of measuring the amount of solid particles entrapped on the filter.

25. A system as claimed in claim 19 wherein said particles are concentrated in a particular portion of said filter.

26. A system as claimed in claim 19 wherein said internal passageway comprises a substantially circular upstream end opening that transitions to a vortex that narrows from the opening end to the down stream end that is proximate to said filter.

27. A method of sampling an ambient atmosphere, or a surface, for solid particles suspended in said ambient atmosphere, or lying on said surface, comprising:

drawing material, comprising gas and solid particles, from said ambient atmosphere, or from said surface, into a larger cross section upstream end of an internal passageway in a cassette;

concentrating said solid particles in said gas as a function of said material being drawn through said internal passageway from said larger cross section upstream end toward a smaller cross section downstream end of said internal passageway;

drawing all of said material, including all of said concentrated solid particles, through at least a portion of a filter disposed at a downstream end of said internal passageway; and measuring the quantity of solid particles trapped by said filter portion during a predetermined time interval.

28. The method claimed in claim 27 further comprising reducing the cross sectional area of said internal passageway from its upstream end to its downstream end and amount sufficient to cause said solid particles to be concentrated.

29. The method as claimed in claim 27 wherein at least a portion of said filter is in direct contact with said downstream end of said internal passageway.

30. The method as claimed in claim 27 further comprising introducing said material to said internal passageway though an entry port of smaller cross section than the cross section of said upstream end of said internal passageway.

31. The method as claimed in claim 30 wherein said entry port comprises a tubing.

* * * * *